United States Patent
Baynham

(10) Patent No.: US 9,655,735 B2
(45) Date of Patent: May 23, 2017

(54) SPINAL DISC PROSTHESIS

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 383 days.

(21) Appl. No.: 14/214,488

(22) Filed: Mar. 14, 2014

(65) Prior Publication Data

US 2014/0277469 A1      Sep. 18, 2014

Related U.S. Application Data

(60) Provisional application No. 61/800,476, filed on Mar. 15, 2013.

(51) Int. Cl.
*A61F 2/44* (2006.01)
*A61F 2/30* (2006.01)

(52) U.S. Cl.
CPC ............ *A61F 2/442* (2013.01); *A61F 2/4425* (2013.01); *A61F 2002/30092* (2013.01); *A61F 2002/30163* (2013.01); *A61F 2002/30387* (2013.01); *A61F 2002/30578* (2013.01); *A61F 2002/30649* (2013.01); *A61F 2002/30822* (2013.01); *A61F 2002/30827* (2013.01); *A61F 2002/30884* (2013.01); *A61F 2002/30904* (2013.01); *A61F 2002/443* (2013.01)

(58) Field of Classification Search
CPC .......... A61F 2/44; A61F 2/442; A61F 2/4425; A61F 2/4455; A61F 2/446; A61F 2/4465; A61F 2/447; A61F 2002/443; A61F 2002/4435; A61F 2002/444

USPC ............................................ 623/17.11–17.16
See application file for complete search history.

(56) References Cited

U.S. PATENT DOCUMENTS

| | | | | |
|---|---|---|---|---|
| 4,759,769 | A * | 7/1988 | Hedman | A61F 2/4425 623/17.13 |
| 5,236,460 | A * | 8/1993 | Barber | A61F 2/441 403/109.7 |
| 5,246,458 | A * | 9/1993 | Graham | A61B 17/1757 606/247 |
| 5,360,430 | A * | 11/1994 | Lin | A61F 2/4425 606/247 |
| 6,063,121 | A * | 5/2000 | Xavier | A61F 2/4425 606/247 |
| 6,106,557 | A * | 8/2000 | Robioneck | A61F 2/44 606/246 |
| 6,190,413 | B1 * | 2/2001 | Sutcliffe | A61F 2/44 606/246 |
| 6,228,118 | B1 * | 5/2001 | Gordon | A61F 2/4425 623/17.11 |
| 6,733,532 | B1 * | 5/2004 | Gauchet | A61F 2/442 606/247 |

(Continued)

*Primary Examiner* — Christian Sevilla
*Assistant Examiner* — Eric S Gibson
(74) *Attorney, Agent, or Firm* — McHale & Slavin, P.A.

(57) ABSTRACT

A spinal implant for insertion between adjacent vertebrae to function as a disc prosthesis. The prosthesis is formed from two plates fastened to adjacent vertebrae facing each other. The facing sides of the plates have a donut shaped cushioning coupler to replicate the displaced disc material. Stabilizing links are positioned along the edge of the plates to prevent over compression of the shaped cushioning coupler in a bending moment. Adjustable mounting brackets are used to secure the implant to the spine.

10 Claims, 4 Drawing Sheets

(56) References Cited

U.S. PATENT DOCUMENTS

| | | | | |
|---|---|---|---|---|
| 6,899,735 B2* | 5/2005 | Coates | A61F 2/44 | |
| | | | 623/17.11 | |
| 7,060,097 B2* | 6/2006 | Fraser | A61F 2/442 | |
| | | | 623/17.11 | |
| 7,105,024 B2* | 9/2006 | Richelsoph | A61F 2/4425 | |
| | | | 623/17.13 | |
| 7,291,173 B2* | 11/2007 | Richelsoph | A61F 2/4425 | |
| | | | 623/17.13 | |
| 7,462,196 B2* | 12/2008 | Fraser | A61F 2/442 | |
| | | | 623/17.11 | |
| 7,811,329 B2* | 10/2010 | Ankney | A61F 2/4405 | |
| | | | 623/17.16 | |
| 7,832,409 B2* | 11/2010 | Richelsoph | A61F 2/4425 | |
| | | | 128/898 | |
| 8,083,796 B1* | 12/2011 | Raiszadeh | A61F 2/442 | |
| | | | 623/17.11 | |
| 8,128,701 B2* | 3/2012 | Kast | A61F 2/442 | |
| | | | 623/17.15 | |
| 8,287,572 B2* | 10/2012 | Bae | A61B 17/846 | |
| | | | 606/279 | |
| 8,353,964 B2* | 1/2013 | Carpenter | A61F 2/442 | |
| | | | 623/17.16 | |
| 8,409,287 B2* | 4/2013 | Braddock, Jr. | A61F 2/4425 | |
| | | | 623/17.15 | |
| 8,496,713 B2* | 7/2013 | Bennett | A61F 2/4425 | |
| | | | 623/17.11 | |
| 8,696,749 B2* | 4/2014 | Lyons | A61F 2/442 | |
| | | | 623/17.12 | |
| 8,911,498 B2* | 12/2014 | Bartish, Jr. | A61F 2/442 | |
| | | | 623/17.14 | |
| 8,998,991 B2* | 4/2015 | Bennett | A61F 2/4425 | |
| | | | 623/17.16 | |
| 9,033,993 B2* | 5/2015 | Bae | A61B 17/1671 | |
| | | | 606/279 | |
| 9,168,152 B2* | 10/2015 | Raiszadeh | A61F 2/442 | |
| 2003/0220691 A1* | 11/2003 | Songer | A61F 2/442 | |
| | | | 623/17.14 | |
| 2004/0225362 A1* | 11/2004 | Richelsoph | A61F 2/4425 | |
| | | | 623/17.13 | |
| 2004/0225363 A1* | 11/2004 | Richelsoph | A61F 2/4425 | |
| | | | 623/17.13 | |
| 2004/0225364 A1* | 11/2004 | Richelsoph | A61F 2/4425 | |
| | | | 623/17.13 | |
| 2004/0243238 A1* | 12/2004 | Arnin | A61F 2/4425 | |
| | | | 623/17.12 | |
| 2004/0249462 A1* | 12/2004 | Huang | A61F 2/441 | |
| | | | 623/17.13 | |
| 2005/0015150 A1* | 1/2005 | Lee | A61F 2/442 | |
| | | | 623/17.12 | |
| 2005/0065611 A1* | 3/2005 | Huppert | A61F 2/4425 | |
| | | | 623/17.15 | |
| 2005/0197702 A1* | 9/2005 | Coppes | A61F 2/441 | |
| | | | 623/17.12 | |
| 2005/0203626 A1* | 9/2005 | Sears | A61F 2/4425 | |
| | | | 623/17.11 | |
| 2005/0228500 A1* | 10/2005 | Kim | A61F 2/442 | |
| | | | 623/17.13 | |
| 2005/0251262 A1* | 11/2005 | De Villiers | A61F 2/4425 | |
| | | | 623/17.14 | |
| 2005/0277938 A1* | 12/2005 | Parsons | A61B 17/70 | |
| | | | 606/291 | |
| 2006/0178745 A1* | 8/2006 | Bartish, Jr. | A61F 2/442 | |
| | | | 623/17.13 | |
| 2006/0178746 A1* | 8/2006 | Bartish, Jr. | A61F 2/4425 | |
| | | | 623/17.13 | |
| 2007/0055378 A1* | 3/2007 | Ankney | A61F 2/4405 | |
| | | | 623/17.15 | |
| 2007/0179615 A1* | 8/2007 | Heinz | A61F 2/4425 | |
| | | | 623/17.12 | |
| 2008/0262620 A1* | 10/2008 | Richelsoph | A61F 2/4425 | |
| | | | 623/17.16 | |
| 2008/0262621 A1* | 10/2008 | Gorek | A61F 2/4465 | |
| | | | 623/17.16 | |
| 2009/0005874 A1* | 1/2009 | Fleischmann | A61F 2/442 | |
| | | | 623/17.16 | |
| 2009/0076610 A1* | 3/2009 | Afzal | A61F 2/442 | |
| | | | 623/17.16 | |
| 2009/0076614 A1* | 3/2009 | Arramon | A61F 2/4425 | |
| | | | 623/17.16 | |
| 2009/0132054 A1* | 5/2009 | Zeegers | A61B 17/0642 | |
| | | | 623/17.16 | |
| 2009/0143861 A1* | 6/2009 | Errico | A61B 17/025 | |
| | | | 623/17.16 | |
| 2009/0182432 A1* | 7/2009 | Zdeblick | A61B 17/1757 | |
| | | | 623/17.16 | |
| 2009/0216330 A1* | 8/2009 | Geisert | A61B 17/1671 | |
| | | | 623/17.16 | |
| 2009/0234456 A1* | 9/2009 | Nycz | A61F 2/442 | |
| | | | 623/17.16 | |
| 2009/0234458 A1* | 9/2009 | de Villiers | A61F 2/30771 | |
| | | | 623/17.16 | |
| 2009/0276051 A1* | 11/2009 | Arramon | A61F 2/4425 | |
| | | | 623/17.16 | |
| 2010/0004746 A1* | 1/2010 | Arramon | A61F 2/4425 | |
| | | | 623/17.15 | |
| 2010/0106251 A1* | 4/2010 | Kast | A61F 2/442 | |
| | | | 623/17.16 | |
| 2010/0204796 A1* | 8/2010 | Bae | A61B 17/846 | |
| | | | 623/17.16 | |
| 2010/0217395 A1* | 8/2010 | Bertagnoli | A61B 17/14 | |
| | | | 623/17.16 | |
| 2010/0228351 A1* | 9/2010 | Ankney | A61B 17/1671 | |
| | | | 623/17.16 | |
| 2010/0234954 A1* | 9/2010 | Justis | A61F 2/4425 | |
| | | | 623/17.12 | |
| 2010/0241231 A1* | 9/2010 | Marino | A61F 2/4455 | |
| | | | 623/17.15 | |
| 2010/0324688 A1* | 12/2010 | Doty | A61F 2/4425 | |
| | | | 623/17.16 | |
| 2011/0040385 A1* | 2/2011 | Biedermann | A61F 2/44 | |
| | | | 623/17.16 | |
| 2011/0077739 A1* | 3/2011 | Rashbaum | A61F 2/4425 | |
| | | | 623/17.16 | |
| 2011/0137421 A1* | 6/2011 | Hansell | A61F 2/4425 | |
| | | | 623/17.16 | |
| 2011/0224793 A1* | 9/2011 | Fortin | A61F 2/44 | |
| | | | 623/17.12 | |
| 2011/0288645 A1* | 11/2011 | Braddock, Jr. | A61F 2/4425 | |
| | | | 623/17.16 | |
| 2012/0022654 A1* | 1/2012 | Farris | A61F 2/44 | |
| | | | 623/17.16 | |
| 2012/0109316 A1* | 5/2012 | Marnay | A61F 2/4425 | |
| | | | 623/17.16 | |
| 2012/0150298 A1* | 6/2012 | Bennett | A61F 2/4425 | |
| | | | 623/17.11 | |
| 2012/0197406 A1* | 8/2012 | Paul | A61B 17/1757 | |
| | | | 623/17.16 | |
| 2012/0215314 A1* | 8/2012 | Bennett | A61F 2/4425 | |
| | | | 623/17.16 | |
| 2012/0239149 A1* | 9/2012 | Zimmers | A61F 2/30744 | |
| | | | 623/17.16 | |
| 2013/0110240 A1* | 5/2013 | Hansell | A61F 2/4425 | |
| | | | 623/17.16 | |
| 2013/0131806 A1* | 5/2013 | Carpenter | A61F 2/442 | |
| | | | 623/17.12 | |
| 2013/0345816 A1* | 12/2013 | Lombardo | A61B 17/025 | |
| | | | 623/17.16 | |
| 2014/0052257 A1* | 2/2014 | Bennett | A61F 2/4425 | |
| | | | 623/17.16 | |
| 2014/0058517 A1* | 2/2014 | Sabatino | A61F 2/4425 | |
| | | | 623/17.16 | |
| 2014/0081406 A1* | 3/2014 | Kellar | A61F 2/32 | |
| | | | 623/18.11 | |
| 2014/0277469 A1* | 9/2014 | Baynham | A61F 2/442 | |
| | | | 623/17.12 | |
| 2014/0296985 A1* | 10/2014 | Balasubramanian | A61F 2/442 | |
| | | | 623/17.16 | |

(56) References Cited

U.S. PATENT DOCUMENTS

| | | | |
|---|---|---|---|
| 2015/0039089 A1* | 2/2015 | Balasubramanian ... | A61F 2/442 623/17.15 |
| 2015/0088259 A1* | 3/2015 | Hewko ................. | A61F 2/4425 623/17.16 |
| 2016/0038303 A1* | 2/2016 | McCombe ............ | A61F 2/4425 623/17.16 |
| 2016/0074170 A1* | 3/2016 | Rogers ................. | A61F 2/4425 623/17.16 |

* cited by examiner

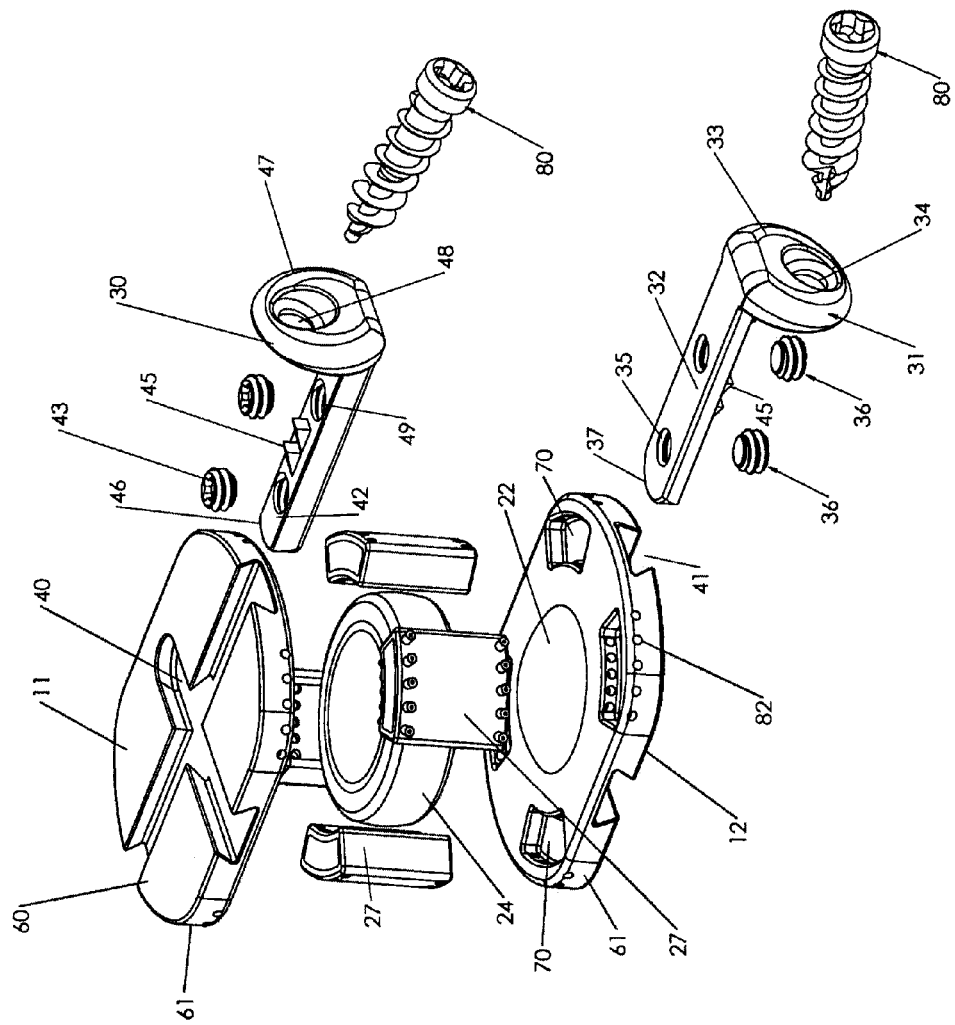
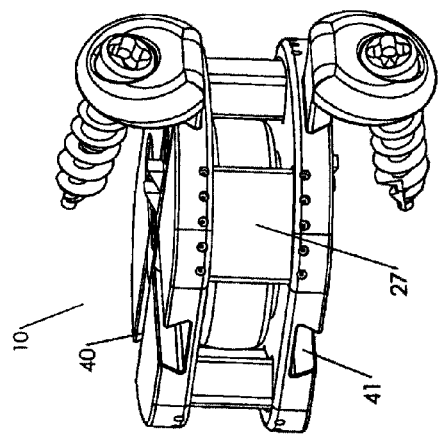
FIG 3
FIG 2

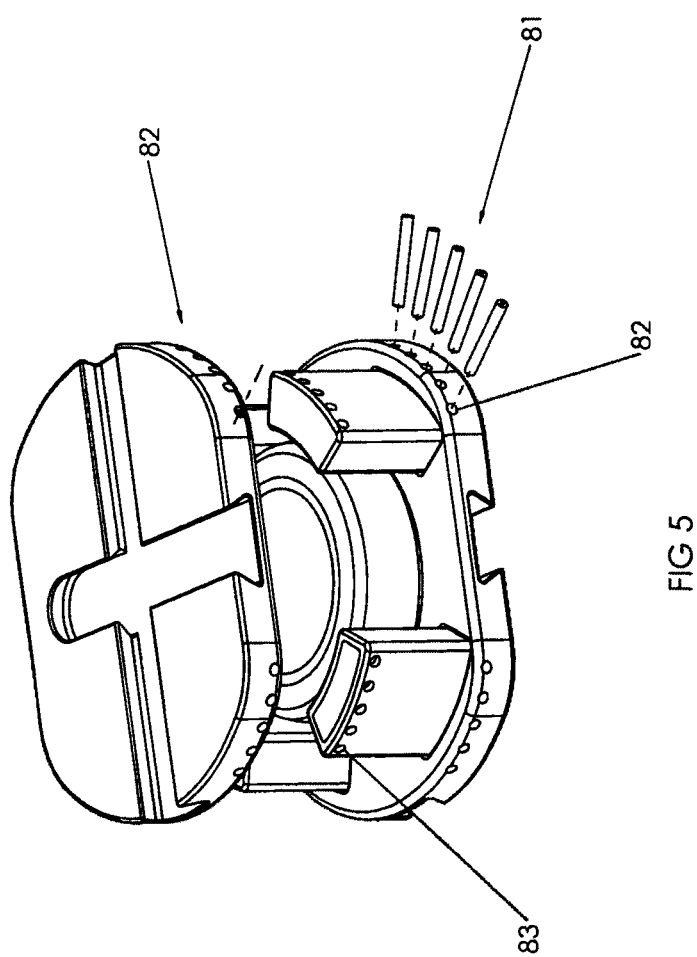

SPINAL DISC PROSTHESIS

PRIORITY CLAIM

In accordance with 37 C.F.R. 1.76, a claim of priority is included in an Application Data Sheet filed concurrently herewith. Accordingly, the present invention claims priority to U.S. provisional patent application Ser. No. 61/800,476, filed on Mar. 15, 2013, entitled "SPINAL DISC PROSTHESIS", the contents of which are hereby expressly incorporated herein by reference.

FIELD OF THE INVENTION

This invention relates to the field of orthopedic surgery and, more particularly, to implants to be placed between vertebrae in the spine.

BACKGROUND OF THE INVENTION

Spinal prosthesis used for replacement of missing or excised disk material to replicate the function of the missing tissue is known. However, improvements in the area are timely and invited. Spinal prosthesis implants are disclosed in U.S. Pat. Nos. 4,759,769; 5,246,458; and 6,228,118.

SUMMARY OF THE INVENTION

Disclosed is a spinal implant for insertion between adjacent vertebrae to function as a disc prosthesis. The prosthesis is formed from two plates fastened to adjacent vertebrae facing each other. The facing sides of the plates have a donut shaped cushioning coupler to replicate the displaced disc material. The cushioning coupler is a compressible elastic hollow body which is secured between the two plates. The hollow body can be filled with an incompressible fluid. In addition, stabilizing links are positioned along the edge of the plates to prevent over compression of the shaped cushioning coupler in a bending moment.

It is an objective of the invention to provide an intervertebral prosthesis wherein undesired tensile stresses under unilateral loads is reduced or eliminated It is another object of the invention to provide a compressible prosthesis which is able to accept edge loading in with a controlled reinforcement.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 2 is a pictorial view of the spinal implant;

FIG. 3 is a pictorial view of the spinal implant and various components thereof;

FIG. 5 is a pictorial view of the spinal implant.

DETAILED DESCRIPTION OF THE INVENTION

Figure 1:
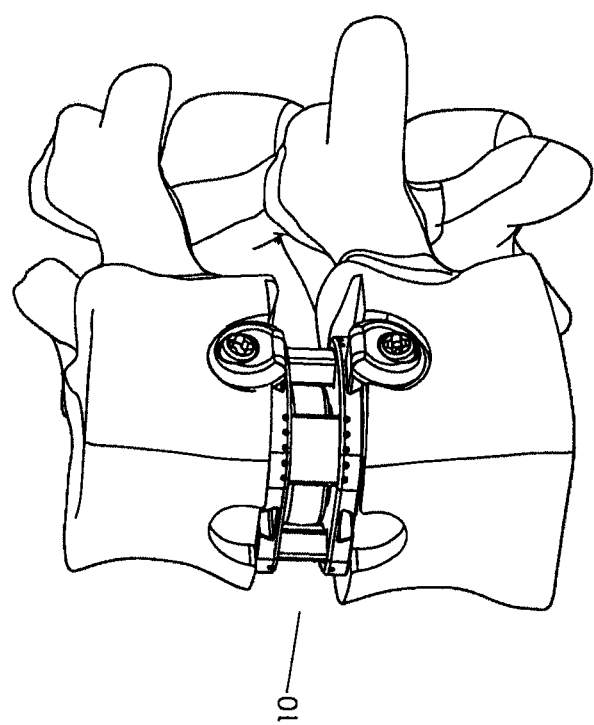
FIG. 1 is a pictorial view of the spinal implant inserted in the intervertebral space.
Figure 4:
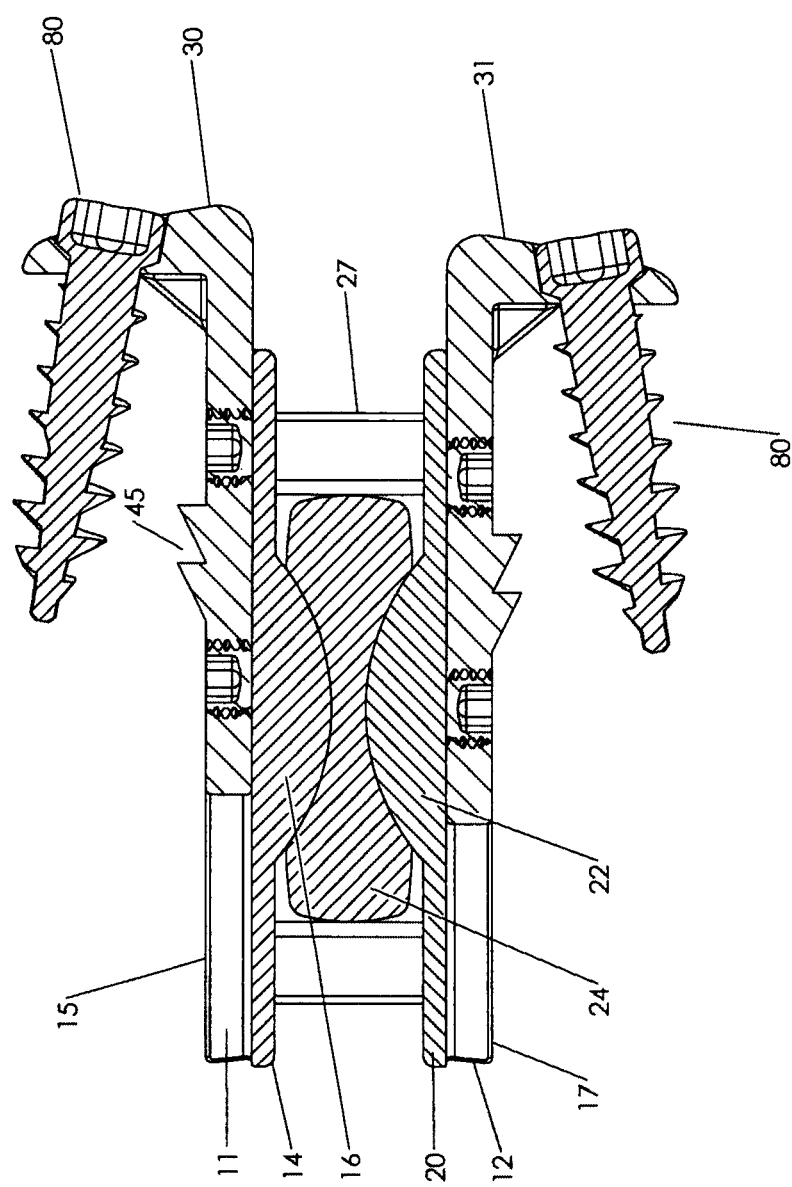
FIG. 4 is a side view of the spinal implant depicting the shaped cushioning coupler.

The spinal implant 10 is inserted in the intervertebral space to replace damaged, missing or excised disk material (FIG. 1). The implant 10 is formed from an upper plate 11 having a first inwardly facing surface 14 with a shaped body 16 and a lower plate 12 having a second inwardly facing surface 20 with a shaped body 22. The facing sides of the plates support a donut shaped cushioning coupler 24 to replicate the displaced disc material (FIGS. 2-4).

The cushioning coupler 24 is a compressible elastic hollow body formed as a toroidal ring secured between the plates. An annular cavity of the hollow body can be filled with an incompressible fluid such as physiological sodium chloride or a silicon oil. Alternatively a highly elastic polymer, for example polyurethane, can be used. With a fluid medium which is incompressible under the occurring loads, the elastic compressible hollow body maintains a constant volume. Under "decentralized" loads, the liquid content in the cavity of the hollow body shifts within the annular cavity and leads to an expansion of the body in that region. Thus, tensile stresses are reduced or even avoided.

In addition, stabilizing links 27 are positioned along four corners of the implant for use in securing the plate 11 and 12 together, but also to prevent over compression of the shaped cushioning coupler 24 in a bending moment (FIGS. 2, 3). The stabilizing links 27 are also made of an elastic or compressible polymer. The links or bushings are comprised of a resilient material with a fiberous laminate skeleton which provides both compression and tension resistance. Excessive bending of the implant can result in the expansion of the body in a radial direction under compressive stress which can be limited if the radial limit of the body is reinforced by a stabilizing links 27 reinforcing means. Compression along one edge results in expansion along an opposite edge, the stabilizing links accommodating this reaction.

Plates 11 and 12 include adjustable mounting brackets or depth stops 30 and 31. The upper plate 11 includes a mounting bracket or depth stop 30 having a base or elongated planar body 42 that is slidable within the recesses, grooves or receptacle 40. Locking screws 43 maintain the base to the receptacle at a position selected by the surgeon. Teeth or sharp protuberances 45 engage the bone and prevent movement upon placement. Similarly, lower plate 12 includes a mounting bracket 31 having a base or planar body 32 that is slidable within receptacle 41. Locking screws 36, maintain the base or planar body 32 to the receptacle 41 at a position selected by the surgeon. As illustrated in FIGS. 1, 2 and 3, the mounting brackets can be positioned at different positions to accommodate the individual situation.

With the above description providing certain details, embodiments of the device(s) are provided.

In preferred embodiments a spinal implant comprises an upper endplate 11, a lower endplate 12, a cushioning coupler 24, a stabilizing linker 27, an adjustable mounting bracket or depth stop 30, 31, a bone screw 80 or combinations thereof (FIG. 3).

In preferred embodiments, the upper 11 and lower endplates 12 comprise a planar surface 60, pointed, rounded or curved 61 edges.

In preferred embodiments, the upper 11 and lower 12 end plates comprise an outward facing surface 15 and 17 respectively, for receiving the depth stop 30, 31 and engaging a vertebra; an inward facing surface 14, 20 for engaging the cushioning coupler 24. The outward facing surfaces of the upper and lower plates comprise one or more receptacles, recesses or grooves 40 for receipt of the depth stop 30, 31.

In other preferred embodiment, the inward facing surface comprises a shaped body 16, 22, the shaped body comprising a convex dome, a concave dome, a shaped protuberance, or a recess, and, one or more slots or recesses 70 for receiving one or more stabilizing linkers 27, the stabilizing linkers 27 being detachably fastened to the upper and lower plates by a pin 81 (FIGS. 3, 4, 5). The stabilizing linkers comprising one or more holes 83, aligned with the holes 82 of the upper and lower endplates (FIGS. 3 and 5). In preferred embodiments, the stabilizing linkers further serve the purpose of a spinal ligament allowing for a degree of movement and stability.

In preferred embodiments, the pins 81 are inserted into one or more holes 82, tunneled horizontally through each plate through to the slot 70, and aligned with a pin receiving aperture 83 in the stabilizing linker 27.

In preferred embodiments, the stabilizing linkers 27 are blocked shaped having planar, curved, concave or a convex surface. However, it is to be understood that these linkers can have any shape or size and can be placed at varying distances and positions from each other, depending on the position of the slots or recesses in the upper and lower plates.

In a preferred embodiment, the cushioning coupler 24 is removable, and is shaped and dimensioned for disposition between the upper 11 and lower 12 endplates, within the confines of the stabilizing linker 27 disposed on the periphery or edges 61 of the upper and lower endplates (FIG. 4).

In preferred embodiments, the cushioning coupler 24 comprises a doughnut or toroid shape, square shape, spherical shape, oval or elliptical shaped. Preferably, the cushioning coupler 24 is toroid shaped. The shaped body 16, 22, can thus be shaped, dimensioned or patterned to accommodate the cushioning coupler 24. The cushioning coupler is optionally fillable with volumetric fluids comprising: saline, gels, latex, polymers, polyethylenes, silicones, polyurethanes, collagen, or hydrogels.

In preferred embodiments, the cushioning coupler 24 is a compressible elastic body.

In another preferred embodiment, the retractable bracket or depth stop 30 comprises an elongated planar body 42 with at least one sharp protuberance 45 disposed on the surface of the planar body 42, the planar surface having a first end 46 for sliding into the recesses or grooves 40 of the outward facing surfaces 15, 17 of the upper 11 and lower 12 endplates, a second end 47 which is perpendicular to the planar body, comprising an aperture 48 for receipt of a bone screw 80 (FIG. 3). Similarly, the retractable bracket or depth stop 31 comprises an elongated planar body 32 with at least one sharp protuberance 45 disposed on the surface of the planar body 32, the planar surface having a first end 37 for sliding into the recesses or grooves 40 of the outward facing surfaces 15, 17 of the upper 11 and lower 12 endplates, a second end 33 which is perpendicular to the planar body, comprising an aperture 34 for receipt of a bone screw 80. The sharp protuberances 45 engage the bone and prevent movement upon placement of the retractable brackets or depth stops 30, 31 (FIG. 3).

In yet another preferred embodiment, the planar body 42, 32 comprises one or more apertures 49, 35 for receipt of a set screw 43, 36 for securing the depth stop or mounting bracket 30, 31 to the upper and lower plates and to fix the position of the depth stop.

In preferred embodiments, the bone screw 80 attaches the device to the intervertebral space.

In other preferred embodiments, the device and components thereof are formed from biocompatible materials, such as titanium, or any conventional material used for surgical implants, such as stainless steel and its many different alloys, titanium alloys, metallic alloys, polymeric materials, plastics, plastic composites, elastic materials, shape memory alloys (e.g. nitinol), shape memory polymers, stainless steel and alloys thereof, thermoplastics, thermoplastic composites, organic polymer thermoplastics, plastics, plastic composites, ceramic or combinations thereof and any other metal or material with the requisite strength and biologically inert properties.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A spinal implant comprising: an upper endplate having an upper surface with a mounting receptacle formed in said upper surface positioned longitudinally and another mounting receptacle formed perpendicular thereto intersecting the upper mounting receptacle, said upper endplate having a upper mounting bracket formed from a first elongated planar body with at least one sharp protuberance disposed on the planar body, the planar body having a first end for sliding into one of the upper endplate mounting receptacles and at least one aperture for receipt of a set screw to secure said upper mounting bracket in a fixed position within said mounting receptacle, and said upper endplate having an inwardly facing surface with multiple recesses, a lower endplate forming a mirror image of said upper endplate defined by a lower surface having one mounting receptacle positioned longitudinally and a second mounting receptacle formed perpendicular thereto intersecting the lower mounting receptacle, said lower endplate having a lower mounting bracket formed from a second elongated planar body with at least one sharp protuberance disposed on the second elongated planar body, the second elongated planar body having a first end for sliding into one of the lower endplate mounting receptacles with at least one aperture for receipt of a set screw for securing the lower mounting bracket in a fixed position within said mounting receptacle, and said lower endplate having an inwardly facing surface with multiple recesses, stabilizing linkers constructed of a resilient material with a fibrous laminate skeleton having a first end positioned within the upper endplate recess detachably secured thereto by a first plurality of pins extending through the skeleton and a lower end positioned within the lower endplate recess detachably secured thereto by a second plurality of pins extending through the skeleton; and a cushioning coupler positioned within a space defined by the stabilizing linkers and said inwardly facing surfaces; wherein said spinal implant is configured to be placed within an intervertebral space and configured to be secured thereto.

2. The spinal implant of claim 1, wherein the upper and lower endplates comprise a planar surface having recesses which form said mounting receptacles and rounded or curved edges along a perimeter of each of said endplate.

3. The spinal implant of claim 1, wherein the inward facing surface has a shaped body, the shaped body comprising a convex dome, a concave dome, a shaped protuberance, or a recess.

4. The spinal implant of claim 3, wherein the pins are inserted into one or more holes, tunneled horizontally through each plate through to the slot, and aligned with a pin receiving aperture in the stabilizing linkers.

5. The spinal implant of claim 1, wherein the stabilizing linkers are block shaped having: planar, curved, concave or a convex surface.

6. The spinal implant of claim 1, wherein the cushioning coupler is removable, and is shaped and dimensioned for disposition between the upper and lower endplates, within the confines of the stabilizing linkers disposed along a periphery of the upper and lower endplates, said pin extending through the skeleton of said linkers and extending into the endplate.

7. The spinal implant of claim 6, wherein the cushioning coupler comprises a doughnut or toroid shape, square shape, spherical shape, oval or elliptical shape.

8. The spinal implant of claim 6, wherein the cushioning coupler is toroid shape.

9. The spinal implant of claim 6, wherein the cushioning coupler is fillable with volumetric fluids selected from the group of: saline, gels, latex, polymers, polyethylenes, silicones, polyurethanes, collagen, or hydrogels.

10. The spinal implant of claim 6, wherein the cushioning coupler is a compressible elastic body.

* * * * *